(12) United States Patent
Lee et al.

(10) Patent No.: US 10,345,243 B2
(45) Date of Patent: Jul. 9, 2019

(54) APPARATUS AND METHOD FOR PROCESSING BIO OPTICAL SIGNAL USING SPREAD SPECTRUM

(71) Applicants: Electronics and Telecommunications Research Institute, Daejeon (KR); Korea Advanced Institute of Science and Technology, Daejeon (KR)

(72) Inventors: Won Kyoung Lee, Daejeon (KR); Ki-Hun Jeong, Daejeon (KR); Moonseong Park, Daejeon (KR)

(73) Assignees: Electronics and Telecommunications Research Institute, Daejeon (KR); Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 15/705,748

(22) Filed: Sep. 15, 2017

(65) Prior Publication Data

US 2018/0328851 A1 Nov. 15, 2018

(30) Foreign Application Priority Data

May 10, 2017 (KR) .......................... 10-2017-0058132

(51) Int. Cl.
| | | |
|---|---|---|
| *G01J 3/44* | (2006.01) | |
| *G01N 21/27* | (2006.01) | |
| *G01N 21/64* | (2006.01) | |
| *G01N 21/65* | (2006.01) | |

(52) U.S. Cl.
CPC ....... *G01N 21/658* (2013.01); *G01N 21/6428* (2013.01); *G01J 2003/4424* (2013.01); *G01N 21/274* (2013.01); *G01N 2201/067* (2013.01); *G01N 2201/06113* (2013.01); *G01N 2201/121* (2013.01)

(58) Field of Classification Search
CPC .................................................... G01N 21/658
See application file for complete search history.

(56) References Cited

U.S. PATENT DOCUMENTS

| | | | |
|---|---|---|---|
| 6,044,285 A | 3/2000 | Chaiken et al. | |
| 8,836,927 B2 | 9/2014 | Lopez et al. | |
| 9,518,916 B1 * | 12/2016 | Pandev | ................ G01N 21/255 |
| 2005/0254047 A1 * | 11/2005 | Brady | ....................... G01J 3/10 |
| | | | 356/301 |
| 2006/0126159 A1 | 6/2006 | Chung et al. | |

(Continued)

OTHER PUBLICATIONS

Van Duyne, Richard P. et al., "Mode-Locked Laser Raman Spectroscopy—A New Technique for the Rejection of Interfering Background Luminescence Signals", *Analytical* Chemistry, vol. 46, No. 2, Feb. 1974 (pp. 213-222).

(Continued)

*Primary Examiner* — Shawn Decenzo

(74) *Attorney, Agent, or Firm* — NSIP Law

(57) ABSTRACT

Disclosed is an apparatus and method for processing a bio optical signal based on a spread spectrum scheme including a demodulator configured to collect a bio optical signal generated in response to an incident beam modulated based on a spreading code being scattered from a target analyte, and remove a noise from the bio optical signal by demodulating the bio optical signal based on the spreading code, wherein the bio optical signal has a correlation with the modulated incident beam.

13 Claims, 10 Drawing Sheets

(56) References Cited

U.S. PATENT DOCUMENTS

| | | |
|---|---|---|
| 2011/0084199 A1 | 4/2011 | Pyo |
| 2016/0223467 A1 | 8/2016 | Suh et al. |
| 2018/0046281 A1* | 2/2018 | Pi .................... A61B 5/02416 |
| 2018/0259553 A1* | 9/2018 | Yang .................... G01Q 60/18 |

OTHER PUBLICATIONS

Praveen, Bavishna B. et al., "Wavelength modulated surface enhanced (resonance) Raman scattering for background-free detection", *Analyst Commpunication,* RSC Publishing, Mar. 2013 (pp. 2816-2820).
Lee, Wonkyoung et al., "Optical Coded SERS Sensors Based on Fiber Optics for Bio-Sensing Applications", *Proceedings of the Annual Biophotonics Conference,* KAIST BioPhotonics Lab, Nov. 2016 (2 pages in English).

* cited by examiner

Molecular vibration

APPARATUS AND METHOD FOR PROCESSING BIO OPTICAL SIGNAL USING SPREAD SPECTRUM

CROSS-REFERENCE TO RELATED APPLICATION(S)

This application claims the priority benefit of Korean Patent Application No. 10-2017-0058132 filed on May 10, 2017, in the Korean Intellectual Property Office, the disclosure of which is incorporated herein by reference for all purposes.

BACKGROUND

1. Field

One or more example embodiments relate to an apparatus and method for processing a bio optical signal for enhancing performance of sensing and imaging technology by increasing an intensity and a sensitivity of the bio optical signal.

2. Description of Related Art

A bio optical signal processing apparatus may perform sensing or imaging on a bio target analyte by analyzing a bio optical signal generated by emitting an incident beam to the bio target analyte. The bio optical signal processing apparatus may include a Raman spectroscopy apparatus and a fluorescence spectroscopy apparatus.

The Raman spectroscopy apparatus may perform sensing or imaging on a cell or a molecule through inelastic Raman scattering occurring by a vibration mode of molecule. In addition, the Raman spectroscopy apparatus is a label-free and non-invasive sensing apparatus for accurately sensing the structural change of a molecule from interaction between electric field of incident photon and molecules.

However, the Raman spectroscopy apparatus may have a disadvantage that a detection sensitivity of the Raman spectroscopy apparatus using a Raman scattering signal is reduced because an intensity of the Raman scattering signal is less than that of an elastic Rayleigh scattering signal having a frequency identical to that of the incident beam.

To overcome such disadvantage, a surface enhanced Raman spectroscopy (SERS) technology has been developed. The SERS technology may enhance an intensity of a Raman scattering signal by increasing an electric field intensity using localized surface Plasmons (LSPs) generated from a metal surface or a metal nanoparticle.

To enhance performance of the Raman spectroscopy apparatus including a SERS apparatus, a resolution of the Raman scattering signal and a performance of a signal-to-noise ratio should be improved by removing various noise signals including a background fluorescence signal. Because the background fluorescence signal is not generated by an interaction with a molecule in a sample to be measured but is a noise occurring in various elements included in an apparatus, the background fluorescence signal may not include information on a molecule to be measured.

The related Raman scattering method (S. Christesen, Proc. SPIE, 2010) may distinguish a Raman scattering signal having high polarization and a fluorescence signal having low polarization by modulating polarization of an incident beam. However, because a degree of polarization of a background fluorescence signal is significant and unstable in real measurement, it is difficult to guarantee a stable function of separating a Raman scattering signal and a noise signal.

Also, the related fluorescence scattering signal processing apparatus may analyze the fluorescence scattering signal generated by performing specific binding on a fluorescent material and a target analyte. However, a performance of a sensing and image technology deteriorates seriously because the related fluorescence scattering signal processing apparatus has difficulty in differentiating the background fluorescence signal and the fluorescence scattering signal generated by performing non-specific binding of an non-target analyte.

Thus, the related fluorescence scattering signal processing apparatus may precisely perform a washing process to prevent a non-target analyte from sticking to a substrate surface for preventing the background fluorescence signal from being generated. However, the washing process is added such that a whole processing process for sensing and imaging becomes complex and there is limitation in representation because a result slightly changes in response to a degree of washing.

Accordingly, an effective method of separating noise signals including the background fluorescence signal from the bio optical signal including the Raman scattering signal to be measured may be requested.

SUMMARY

An aspect provides an apparatus and method of enhancing a performance of a sensing and imaging technology of a bio optical signal processing apparatus by increasing a resolution and a signal-to-noise ratio of a bio optical signal and removing various system noise signals including a background fluorescence signal.

According to an aspect, there is provided a bio optical signal processing apparatus including a modulator configured to modulate an incident beam based on a spreading code and emit the modulated incident beam to a target analyte, wherein the modulated incident beam is scattered from the target analyte and generates a bio optical signal having a correlation with the modulated incident beam, and the bio optical signal is demodulated based on the spreading code to remove a noise from the bio optical signal.

The modulator may be configured to modulate the incident beam using a frequency being greater than a frequency of an auto-fluorescence signal in response to the bio optical signal corresponding to a Raman scattering signal.

The modulator may be configured to determine a modulation speed of the incident beam based on an amount of life time of the bio optical signal.

A width of a wavelength change in the incident beam and a width of an intensity change in the incident beam may be determined based on a type of the bio optical signal.

The bio optical signal demodulated based on the spreading code to remove the noise from the bio optical signal may have a signal-to-noise ratio in proportion to a length of the spreading code.

According to another aspect, there is provided a bio optical signal processing apparatus including a demodulator configured to collect a bio optical signal generated in response to an incident beam modulated based on a spreading code being scattered from a target analyte, and remove a noise from the bio optical signal by demodulating the bio optical signal based on the spreading code, wherein the bio optical signal has a correlation with the modulated incident beam.

The demodulator may be configured to determine a demodulation speed of the bio optical signal based on an amount of life time of the bio optical signal.

The bio optical signal demodulated based on the spreading code may have a signal-to-noise ratio in proportion to a length of the spreading code.

According to still aspect, there is provided a bio optical signal processing apparatus including a modulator configured to modulate an incident beam based on a spreading code and emit the modulated incident beam to a target analyte, and a demodulator configured to collect a bio optical signal generated in response to the modulated incident beam being scattered from the target analyte, and remove a noise from the bio optical signal by demodulating the bio optical signal based on the spreading code, wherein the bio optical signal has a correlation with the modulated incident beam.

According to further aspect, there is provided a bio optical signal processing method including modulating an incident beam based on a spreading code and emitting the modulated incident beam to a target analyte, wherein the modulated incident beam is scattered from the target analyte and generates a bio optical signal having a correlation with the modulated incident beam, and the bio optical signal is demodulated based on the spreading code to remove a noise from the bio optical signal.

The modulating may include modulating the incident beam using a frequency being greater than a frequency of an auto-fluorescence signal in response to the bio optical signal corresponding to a Raman scattering signal.

The modulating may include determining a modulation speed of the incident beam based on an amount of life time of the bio optical signal.

A width of a wavelength change in the incident beam and a width of an intensity change in the incident beam may be determined based on a type of the bio optical signal.

The bio optical signal demodulated based on the spreading code to remove the noise from the bio optical signal may have a signal-to-noise ratio in proportion to a length of the spreading code.

According to still another aspect, there is provided a bio optical signal processing method including collecting a bio optical signal generated in response to an incident beam modulated based on a spreading code being scattered from a target analyte, and removing a noise from the bio optical signal by demodulating the bio optical signal based on the spreading code, wherein the bio optical signal has a correlation with the modulated incident beam.

The removing of the noise may include determining a demodulation speed of the bio optical signal based on an amount of life time of the bio optical signal.

The bio optical signal demodulated based on the spreading code may have a signal-to-noise ratio in proportion to a length of the spreading code.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Hereinafter, some example embodiments will be described in detail with reference to the accompanying drawings. A method of processing a bio optical signal may be performed by a bio optical signal processing apparatus.

Figure 1:
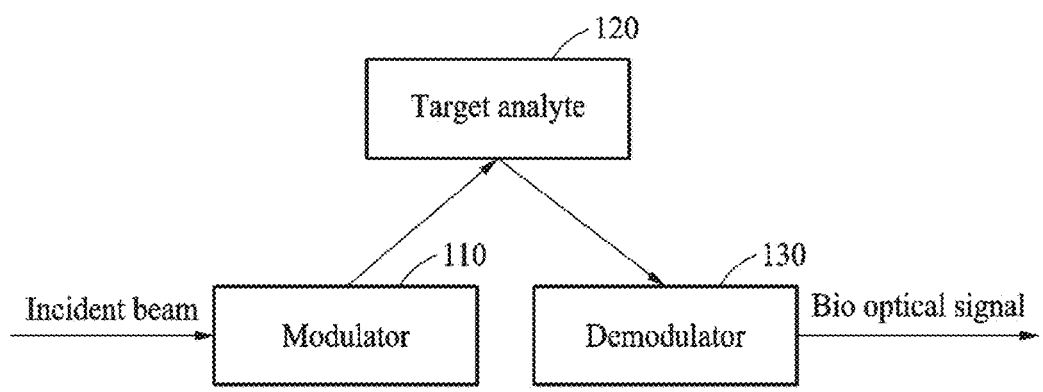
FIG. 1 is a block diagram illustrating a bio optical signal processing apparatus according to an example embodiment.

FIG. 1 is a block diagram illustrating a bio optical signal processing apparatus according to an example embodiment.

As illustrated in FIG. 1, a bio optical signal processing apparatus 100 includes a modulator 110 and a demodulator 130.

The modulator 110 may modulate an incident beam incident to the modulator 110 based on a spreading code. The modulator 110 may allow the modulated incident beam to be incident to a target analyte 120. That is, the modulator 110 may spread a spectrum of the incident beam to be emitted to the target analyte 120.

Here, the modulated incident beam may be scattered from the target analyte 120 to generate a bio optical signal. An attribute of the bio optical signal is different from that of the incident beam, but the bio optical signal may have a relatively high correlation. Detailed description of a correlation between the bio optical signal and the incident beam is provided with reference to FIG. 5.

Also, the bio optical signal includes at least one of a Raman scattering signal, a fluorescence scattering signal, or a Rayleigh scattering signal.

Here, the Raman scattering signal may be an optical signal generated in response to a molecular vibration of a target analyte to which an incident beam is emitted. A wavelength of the Raman scattering signal may be determined based on a vibration energy of the molecule, and an amount of life time of the Raman scattering signal may be less than an amount of life time of each of the fluorescent scattering signal and the Rayleigh scattering signal. Also, the modulator 110 may modulate the incident beam using a modulation frequency greater than that of an auto-fluorescence signal using a microhertz unit. For example, the modulator 110 may modulate the incident beam using a modulation frequency greater than or equal to 1 microhertz. The auto-fluorescence signal is a fluorescence signal generated from a target analyte regardless of a fluorescent material, and is different from the fluorescence scattering signal. Unlike the fluorescence scattering signal classified as a bio optical signal, the auto-fluorescence signal may be classified as a noise.

In addition, the Rayleigh scattering signal may be an optical signal generated by Rayleigh scattering occurring by a wavelength of the incident beam and an atmospheric particle. A wavelength of the Rayleigh scattering signal is identical to the wavelength of the incident beam, and an amount of life time of the Rayleigh scattering signal may be less than that of the fluorescence scattering signal and greater than that of the Raman scattering signal.

Figure 3:
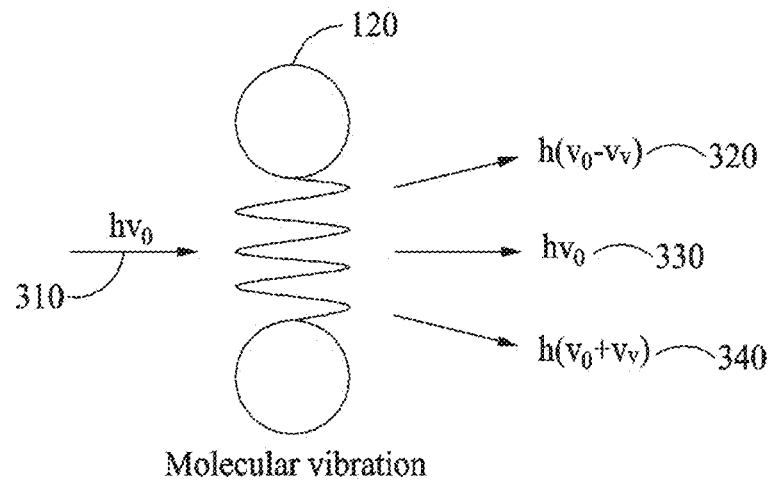
FIG. 3 illustrates a bio optical signal scattered by a target analyte according to an example embodiment.

Detailed description of a relationship between the Raman scattering signal and the Rayleigh scattering signal is provided with reference to FIG. 3.

The fluorescence scattering signal may be an optical signal generated in response to the incident beam being emitted to a fluorescent material applied to the target analyte 120. Here, the wavelength of the fluorescence scattering signal may be determined based on a wavelength of a light source to be incident and the fluorescent material, and the amount of life time of the fluorescence scattering signal may be greater than the amount of life time of each of the Raman scattering signal and the Rayleigh scattering signal.

In addition, the modulator 110 may determine a modulation speed of the incident beam based on an amount of life time of the bio optical signal. In more detail, the modulator 110 may decrease the modulation speed of the incident beam as the amount of life time of the bio optical signal is great, and may increase the modulation speed of the incident beam as the amount of life time of the bio optical signal is less. For example, an amount of life time is great in an order of the fluorescence scattering signal, the Rayleigh scattering signal, and the Raman scattering signal and thus, the modulation speed of the incident beam for using the Raman scattering signal as the bio optical signal may be faster than the modulation speed of the incident beam for using the Rayleigh scattering signal as the bio optical signal. Also, the modulation speed of the incident beam for using the Rayleigh scattering signal as the bio optical signal may be faster than the modulation speed of the incident beam for using the fluorescence scattering signal as the bio optical signal.

Also, a width of a wavelength change and a width of an intensity change in the modulated incident beam or the incident beam incident to the modulator 110 may be determined based on a type of the bio optical signal.

In more detail, a width of a wavelength change and a width of an intensity change in an incident beam for using the Raman scattering signal as the bio optical signal may be less than a width of a wavelength change and an intensity change in an incident beam for using the fluorescence scattering signal or the Rayleigh scattering signal as the bio optical signal. For example, the width of wavelength change in the incident beam for using the Raman scattering signal as the bio optical signal may be less than or equal to 1 nanometer.

The width of the wavelength change and the width of the intensity change in the incident beam for using the Rayleigh scattering signal as the bio optical signal may be greater than the width of the wavelength change and the width of the intensity change in the incident beam for using the Raman scattering signal as the bio optical signal, and may be less than the width of the wavelength change and the width of the intensity change in the incident beam for using the fluorescence scattering signal as the bio optical signal. In addition, the width of the wavelength change and the width of the intensity change in the incident beam for using the fluorescence scattering signal as the bio optical signal may be greater than the width of the wavelength change and the width of the intensity change in the incident beam for using the Raman scattering signal or the Rayleigh scattering signal as the bio optical signal.

A substrate to which the target analyte 120 is to be deposited may be a surface enhanced Raman scattering substrate having a surface to which a metal thin film or a metal nanoparticle is added. Here, because of an electric field intensity increased by an interference between an incident beam and a surface plasmon polariton (SPP) occurring on the surface of the surface enhanced Raman scattering substrate may be reflected by the target analyte 120 or penetrate the target analyte 120, an intensity of the Raman scattering signal is increased.

The target analyte 120 may be a bio target analyte to be analyzed based on a bio optical signal processing method. The target analyte 120 may be deposited on a substrate or may be provided in a solution state. For example, a target analyte may be a cell, a molecule, a protein, a portion of a living organism, or an organism such as a virus.

Also, a substrate to which the target analyte 120 is to be deposited or a process for the target analyte 120 may be determined based on the bio optical signal to be processed. For example, when the Raman scattering signal is used as the bio optical signal, the substrate to which the target analyte 120 is to be deposited may be a surface enhanced Raman scattering substrate having a surface to which the metal thin film or the metal nanoparticle is added. Here, because of the electric field intensity increased by the interference between the incident beam and the SPP occurring on the surface of the surface enhanced Raman scattering substrate may be reflected by the target analyte 120 or penetrate the target analyte 120, an intensity of the Raman scattering signal is increased.

When the fluorescence scattering signal is used as the bio optical signal, the target analyte 120 to which the fluorescent material is applied may be deposited on the substrate. Here, the fluorescence scattering signal may be generated in response to the modulated incident beam being reflected by the fluorescent material or penetrating the fluorescent material applied to the target analyte 120.

The demodulator 130 may collect the bio optical signal generated in response to the modulated incident beam being reflected by the target analyte 120 or penetrating the target analyte 120. The demodulator 130 may output the bio optical signal from which a noise is removed by demodulating the collected bio optical signal based on a spreading code identical to the spreading code used by the modulator 110.

Here, the modulator 130 may determine a demodulation speed of the bio optical signal based on the amount of life time of the bio optical signal. In detail, the demodulator 130 may decrease the demodulation speed of the bio optical signal as the amount of life time of the bio optical signal is great, and increase demodulation speed of the bio optical signal as the amount of life time of the bio optical signal is less. For example, an amount of life time is great in an order of the fluorescence scattering signal, the Rayleigh scattering signal, and the Raman scattering signal and thus, a speed of demodulation of the Raman scattering signal performed by the demodulator 130 may be faster than a demodulation speed of the Rayleigh scattering signal. Also, a speed of demodulation of the Rayleigh scattering signal performed by the demodulator 130 may be faster than the demodulation speed of the fluorescence scattering speed.

The present disclosure may enhance performance of a sensing and imaging technology of the bio optical signal processing apparatus by removing system noises including a background fluorescence signal of various causes and increasing a resolution power and a signal-to-noise ratio of the bio optical signal.

Figure 2:
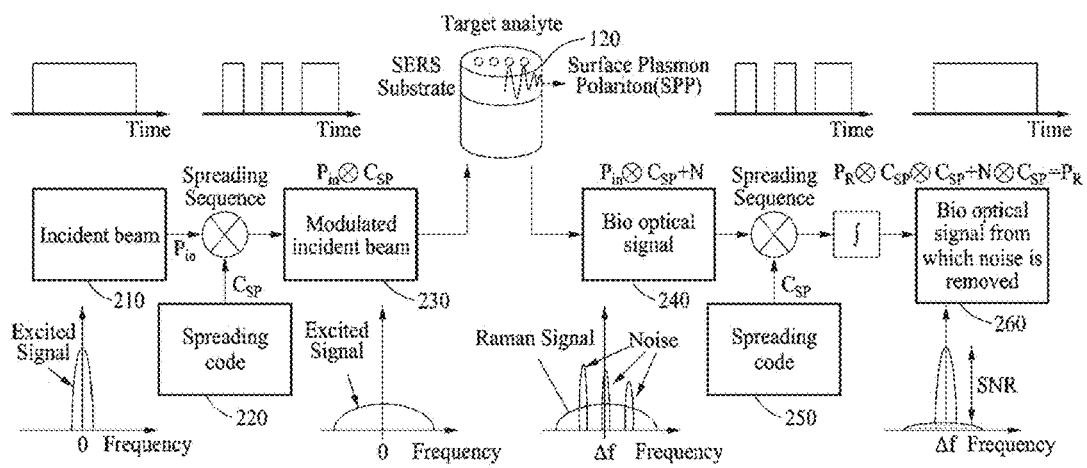
FIG. 2 illustrates an operation of a bio optical signal processing apparatus according to an example embodiment.

FIG. 2 illustrates an operation of a bio optical signal processing apparatus according to an example embodiment.

The modulator 110 modulates an incident beam 210 based on a spreading code 220 to output a modulated incident beam 230. For example, the spreading code 220 may be one of a pseudorandom noise (PN) code, a Golay code, a simplex code, and a hybrid code.

Here, the PN code may include 0 and 1 for spreading a band of the incident beam 210, and the Golay code may remove a sidelobe using two PN codes. The simplex code may use a Hadamard matrix for enhancing performance even when a code length is relatively short, and the hybrid code may be a combination of the simplex code and the Golay code.

In addition, the spectrum of the incident beam may be spreaded widely by modulating intensity of the incident beam according to PN codes, as illustrated in FIG. 2.

The modulated incident beam 230 may be incident to the target analyte 120 deposited on a substrate. The modulated incident beam 230 may be scattered from the target analyte 120 and converted into a bio optical signal 240. Here, the bio optical signal 240 output from the target analyte 120 may include a least one of a Raman scattering signal, a fluorescence scattering noise, or a Rayleigh scattering noise, and a noise occurring due to various causes.

A spectrum of the Raman scattering signal, the fluorescence scattering signal, or the Rayleigh scattering signal is spread similar to the modulated incident beam 230, but a spectrum of the noise is not spread. Thus, the bio optical signal 240 may include the Raman scattering signal, the fluorescence scattering signal, or the Rayleigh scattering signal of which the band is spread as illustrated in FIG. 2, and at least one of a noise of which a band is narrow and an optical signal intensity is great or a noise of which a band is wide and an optical signal intensity is low.

The demodulator 130 may collect the bio optical signal 240. Also, the demodulator 130 may demodulate the bio optical signal 240 based on a spreading code 250. Here, the spreading code 250 may be identical to the spreading code 220 of the modulator 120.

The Raman scattering signal, the fluorescence scattering signal, or the Rayleigh scattering signal included in the bio optical signal 240 may have an attribute differing from that of the modulated incident beam 230, but have a relatively great correlation. Also, a spectrum of the Raman scattering signal, the fluorescence scattering signal, or the Rayleigh scattering signal included in the bio optical signal 240 is spread as illustrated in FIG. 2. Thus, when the bio optical signal 240 is demodulated based on the spreading code 250 identical to the spreading code 220 used to modulate the incident beam 210, the spectrum of the Raman scattering signal, the fluorescence scattering signal, or the Rayleigh scattering signal is recovered and an optical signal intensity corresponding to a frequency increases such that the bio optical signal 240 is demodulated in an identical form of the incident beam 210. A bandwidth of the noise included in the bio optical signal 240 collected by the demodulator 130 may be spread to be close to 0 by the spreading code 250, such that the noise is removed.

That is, the demodulator 130 may output a bio optical signal 260 from which the noise is removed by demodulating the bio optical signal 240 based on the spreading code 250 and removing the noise by spreading the spectrum of noise.

FIG. 3 illustrates a bio optical signal scattered by a target analyte according to an example embodiment.

When a modulated incident beam 310 is incident to the target analyte 120, the modulated incident beam 310 is scattered by the target analyte 120 such that a first Raman scattering signal (stokes) 320, a Rayleigh scattering signal 330, and a second Raman scattering signal (anti-stokes) 340 are output as illustrated in FIG. 3.

A frequency of the first Raman scattering signal 320 is less than a frequency of the second Raman scattering signal 350, and a wavelength of the first Raman scattering signal 320 is behind a wavelength of the second Raman scattering signal 350. In an example, an intensity of the first Raman scattering signal 320 may be greater than an intensity of the second Raman scattering signal 350.

Thus, when a Raman scattering signal is used as a bio optical signal, the demodulator 130 may demodulate the first Raman scattering signal 320 among the first Raman scattering signal 320 and the second Raman scattering signal 350.

When a fluorescent material is applied to a target analyte, the modulated incident beam 310 may be scattered from the fluorescent material and a fluorescence scattering signal may be output. Here, the first Raman scattering signal 320, the Rayleigh scattering signal 330, the second Raman scattering signal 340, and the fluorescence scattering signal are output together, but the demodulator 130 may demodulate the fluorescence scattering signal only in lieu of demodulating the first Raman scattering signal 320, the Rayleigh scattering signal 330, and the second Raman scattering signal 340 because intensities of the first Raman scattering signal 320, the Rayleigh scattering signal 330, and the second Raman scattering signal 340 are less than an intensity of the fluorescence scattering signal.

The fluorescence scattering signal may be output to be a frequency identical to that of the Rayleigh scattering signal 330 or a frequency between the first Raman scattering signal 320 and the Rayleigh scattering signal 330. Here, the fluorescence scattering signal may be generated in response to the fluorescent material absorbing an energy of the modulated incident beam 310 when the fluorescent material is applied to the target analyte as a label. Because the fluorescence scattering signal is generated in response to the fluorescent material absorbing the energy of the modulated incident beam 310, a sensitivity of the fluorescence scattering signal may be less than that of the Raman scattering signal generated in response to a molecular vibration.

Figure 4:
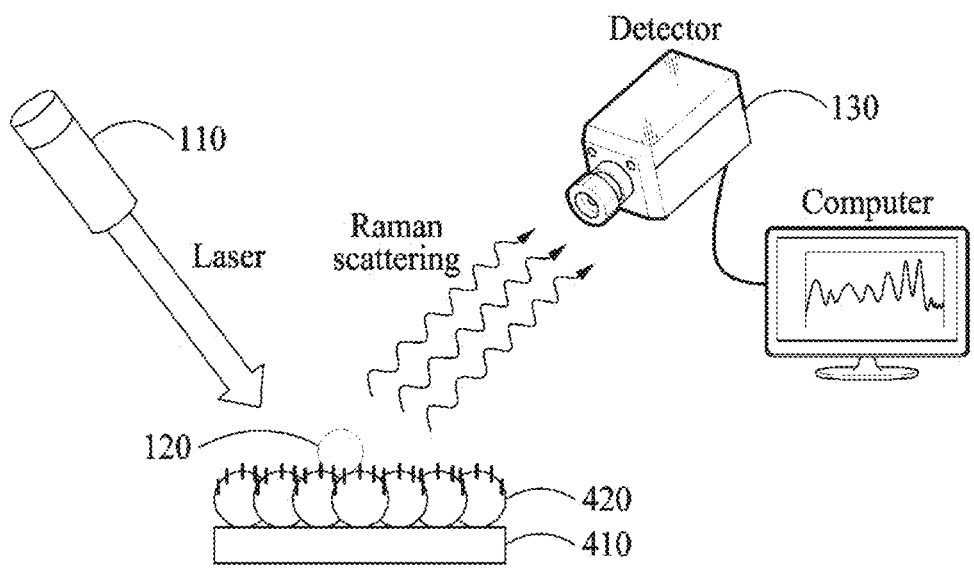
FIG. 4 illustrates a bio optical signal processing apparatus for processing a Raman scattering signal according to an example embodiment.

FIG. 4 illustrates a bio optical signal processing apparatus for processing a Raman scattering signal according to an example embodiment.

The target analyte 120 may be deposited on a surface enhanced Raman scattering substrate 410 having a surface to which a metal nanoparticle 420 is added as illustrated in FIG. 4.

When the modulator 110 allows a modulated incident beam to be incident to the target analyte 120, because of an intensity of an electric field increased by an interference between the modulated incident beam and a surface plasmon polariton (SPP) occurring on the metal nanoparticle 420, an intensity of a Raman scattering signal generated in response to a molecular vibration of the target analyte 120 may increase.

In addition, the demodulator 130 may collect the Raman scattering signal generated from the target analyte 120 and demodulate the Raman scattering signal based on a spreading code identical to that of the modulator 110.

Figure 5:
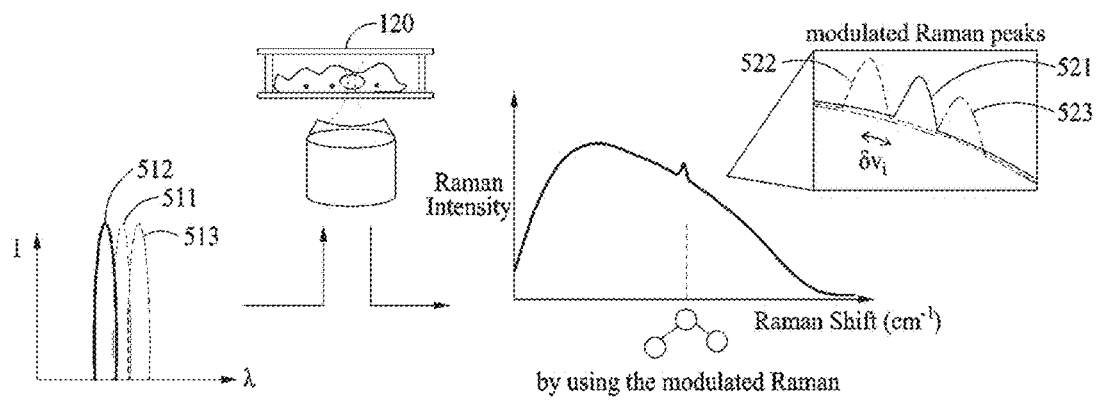
FIG. 5 illustrates a correlation between an incident beam and a Raman scattering signal according to an example embodiment.

FIG. 5 illustrates a correlation between an incident beam and a Raman scattering signal according to an example embodiment.

Raman signals can closely follow the high-frequency modulation of the excited light, while the autofluorescence cannot follow high-frequency modulation owing to its long lifetime. Other noises such as system noise, external interference, and non-target scattering have no correlation with the excited signal.

When the peak wavelength of the incident beam shifts from a reference numeral 511 to a reference numeral 512, peak wavelength band of the Raman scattering signal also shifts from a reference numeral 521 to a reference numeral 522. When the peak wavelength of the incident beam shifts from the reference numeral 511 to a reference numeral 513, the peak wavelength of the Raman scattering signal also shifts from the reference numeral 521 to a reference numeral 523.

Although the incident beam and the Raman scattering signal are optical signals having different features, the Raman scattering signal has a correlation that the Raman scattering signal changes in response to the incident beam changing as illustrated in FIG. 5 and thus, the Raman scattering signal is demodulated based on a spreading code used to modulate the incident beam.

Figure 6:
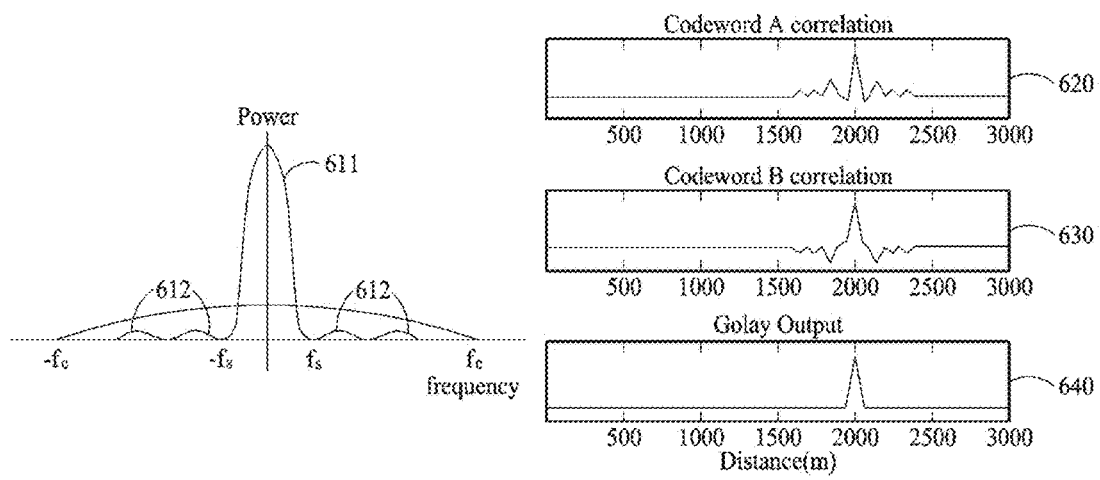
FIG. 6 illustrates an incident beam modulated based on a spreading code according to an example embodiment.

FIG. 6 illustrates an incident beam modulated based on a spreading code according to an example embodiment.

The incident beam includes a main lobe 611 based on an optical signal emitted in a direction of a main beam and side lobes 612 based on an optical signal emitted in another direction other than the direction of the main beam. Here, the side lobes 612 may cause a noise.

A Golay code among spreading codes used by the modulator 110 and the demodulator 130 includes a first code and a second code for removing the side lobes 612. As illustrated in FIG. 6, the main lobe 611 of an incident beam 620 modulated based on the first code by the modulator 110 is identical to that of an incident beam 630 modulated based on the second code, but intensities of the side lobes 612 may have different directions.

A side lobe included in the incident beam 620 modulated based on the first code may be offset by a side lobe included in the incident beam 630 modulated based on the second code. Thus, an incident beam modulated using a Golay code as a spreading code may be in a state in which a side lobe is removed from the incident beam 640 as illustrated in FIG. 6.

Figure 7:
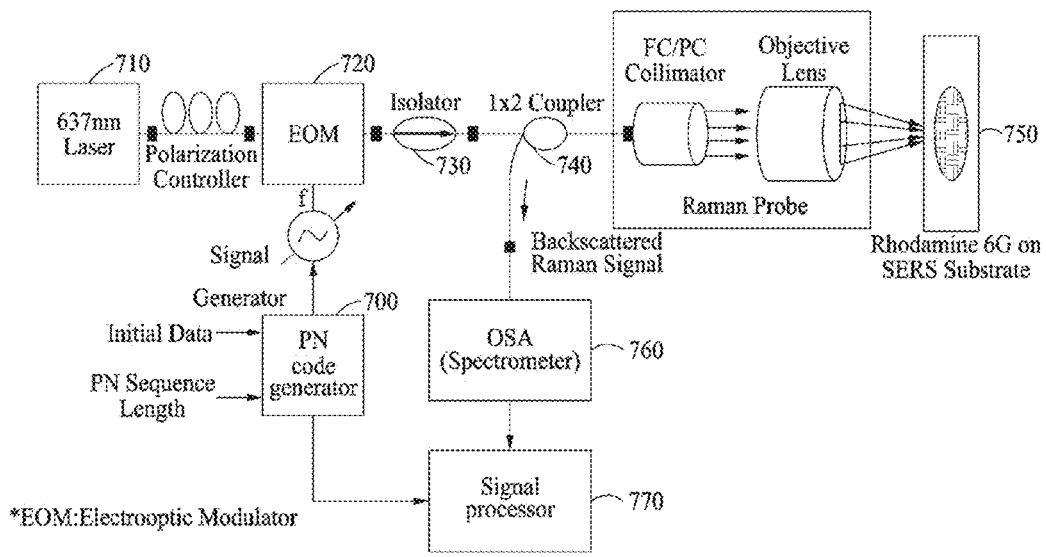
FIG. 7 illustrates a bio optical signal processing apparatus according to an example embodiment.

FIG. 7 illustrates a bio optical signal processing apparatus according to an example embodiment.

A pseudorandom noise (PN) code generator 700 may generate a PN code as a spreading code for spreading a spectrum of an incident beam. For example, the PN code generator 700 generates a PN code having a [1 0 0 1 0 1 1] pattern and a length corresponding to 7. The PN code generator 700 may generate one of a Golay code, a simplex code, and a hybrid code as a spreading code.

An electro-optic modulator (EOM) 720 may modulate an incident beam generated from a continuous wave (CW) laser 710 of which a peak wavelength is 637 nanometers based on the PN code generated by the PN code generator 700. Here, the EOM 720 may correspond to the modulator 110.

An isolator 730 may prevent a Raman scattering signal backscattered by a target analyte 750 from proceeding toward the CW laser 710.

A 1×2 coupler 740 may classify an incident beam modulated by the EOM 720 and incident through the isolator 730 and the Raman scattering signal backscattered by the target analyte 750. Here, the incident beam incident to the 1×2 coupler 740 through the isolator 730 may proceed toward the target analyte 750. In addition, the Raman scattering signal backscattered by the target analyte 750 may proceed toward an optical spectrum analyzer (OSA) 760 by the 1×2 coupler 740.

A collimator and an objective lens may control the Raman scattering signal and the incident beam incident from the EOM 720 through the isolator 730 such that the incident beam and the Raman scattering signal are focused on the target analyte 750.

A signal processor 770 may demodulate the Raman scattering signal passing through the OSA 760 based on the PN code generated by the PN code generator 700. Here, the signal processor 770 may correspond to the demodulator 130.

Figure 8:
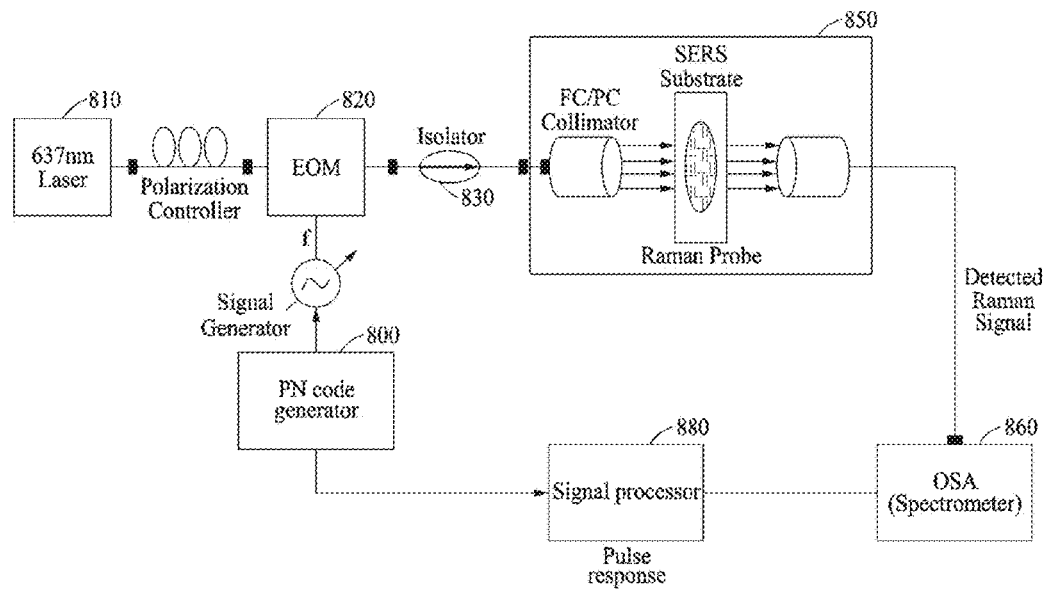
FIG. 8 illustrates a bio optical signal processing apparatus according to another example embodiment.

FIG. 8 illustrates a bio optical signal processing apparatus according to another example embodiment.

A Raman scattering signal may be output to penetrate a target analyte other than to be reflected by the target analyte as illustrated in FIG. 8. FIG. 8 illustrates a structure of the bio optical signal processing apparatus using a Raman scattering signal that penetrates the target analyte.

A pseudorandom noise (PN) code generator 800 generates a PN code as a spreading code for spreading a band of an incident beam. Also, the PN code generator 800 may generate one of a Golay code, a simplex code, and a hybrid code as a spreading code.

An electro-optic modulator (EOM) 820 may modulate an incident beam generated from a continuous wave (CW) laser 810 of which a peak wavelength is 637 nanometers based on the PN code generated by the PN code generator 800. Here, the EOM 820 may correspond to the modulator 110.

An isolator 830 may prevent a Raman scattering signal backscattered by a target analyte 850 from proceeding toward the CW laser 810.

A collimator and an objective lens may control the incident beam incident from the EOM 820 through the isolator 830 such that the incident beam is focused on the target analyte 850.

An optical spectrum analyzer (OSA) 860 may transfer, to a signal processor 880, the Raman scattering signal output in a direction opposite to that of the incident beam emitted to the target analyte 650.

The signal processor 880 may demodulate the Raman scattering signal passing through the OSA 860 based on the PN code generated by the PN code generator 800. Here, the signal processor 870 may correspond to the demodulator 130.

Figure 9:
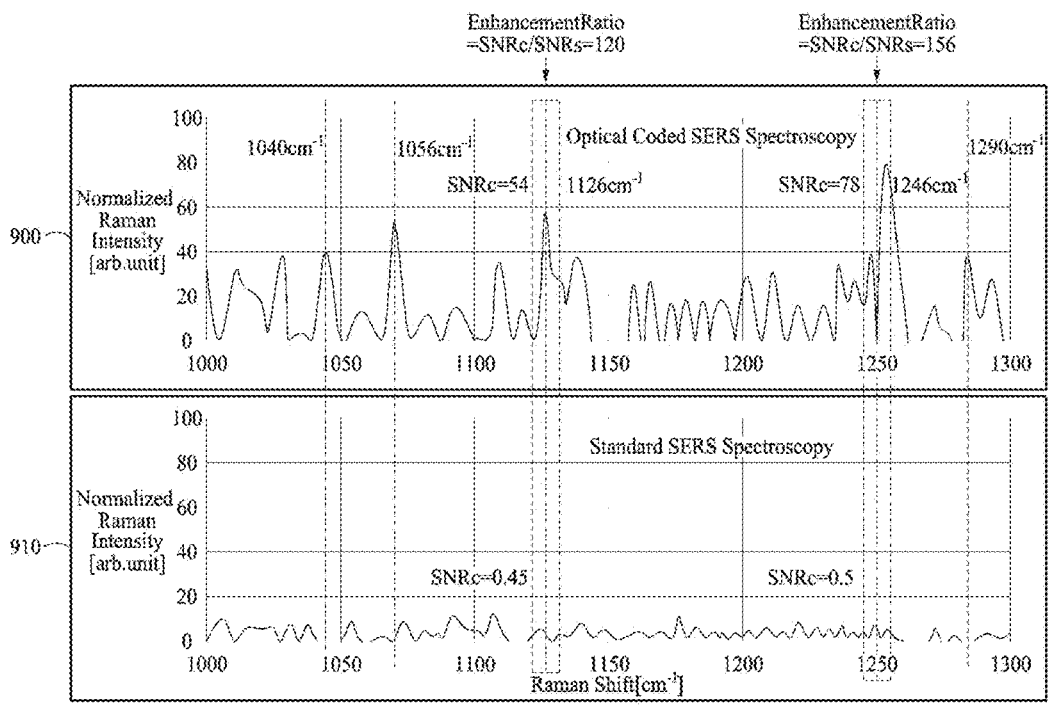
FIG. 9 illustrates a result of measuring a signal-to-noise ratio of a bio optical signal processing method according to an example embodiment.

FIG. 9 illustrates a result of measuring a signal-to-noise ratio of a bio optical signal processing apparatus according to an example embodiment.

An intensity of a Raman scattering signal may be greater with respect to a signal-to-noise ratio 900 of the bio optical signal processing method than a signal-to-noise ratio 910 of the conventional method. For example, at 1246 cm$^{-1}$ of a Raman shift, the signal-to-noise ratio 900 of the bio optical signal processing method is 156 times greater than the signal-to-noise ratio 910 of the conventional method.

Figure 10:
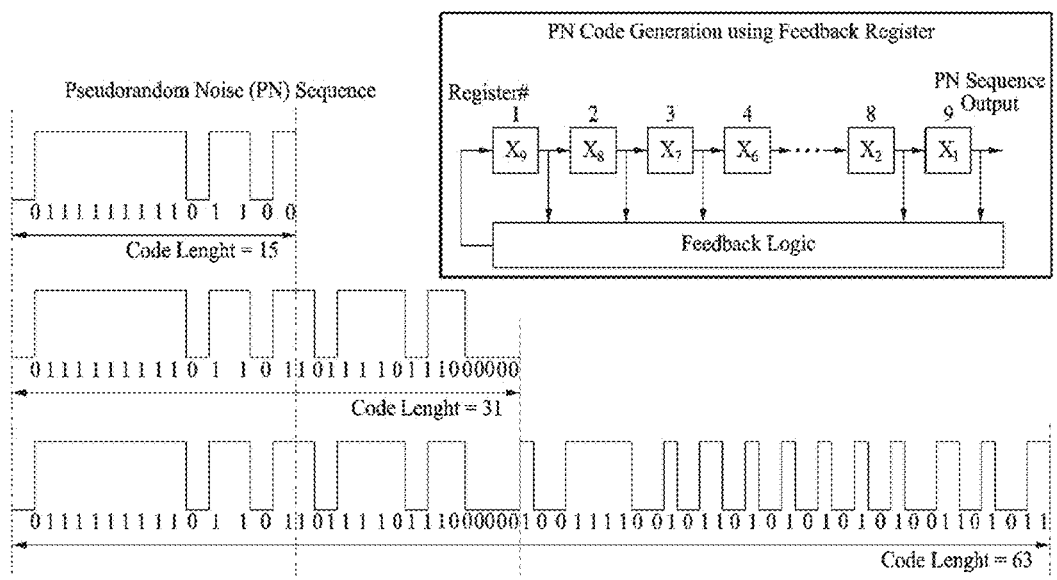
FIG. 10 illustrates a spreading code pattern according to an example embodiment.

FIG. 10 illustrates a spreading code pattern according to an example embodiment.

As a length of a pseudorandom noise (PN) code corresponding to a spreading code increases, spreads of spectrum of an incident beam, a Raman scattering signal, and a noise may increase. The incident beam and the Raman scattering signal may be demodulated by the demodulator 130 even when the bands of the incident beam and the Raman scattering signal are spread. However, a more number of noises may be removed as the band of noise is spread. Thus, the modulator 110 and the demodulator 130 may more effectively remove the noise in a process of demodulating the Raman scattering signal by increasing the length of the spreading code in use.

Figure 11:
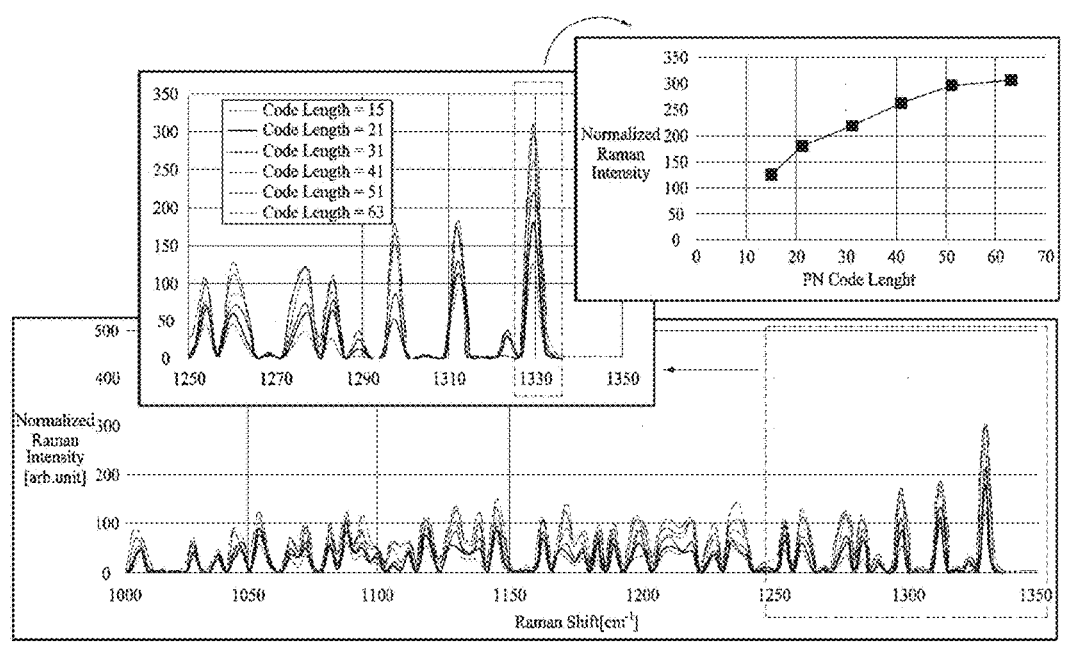
FIG. 11 illustrates a result of measuring a signal-to-noise ratio based on a change in a length of a spreading code according to an example embodiment.

Here, the modulator 110 and the demodulator 130 may increase a length of the PN code corresponding to the spreading code as illustrated in FIG. 10. Here, a signal-to-noise ratio of the Raman scattering signal based on a change in a spreading code may be identical to that of FIG. 11. Referring to FIG. 11, as a length of a spreading code increases, a signal-to-noise ratio may increase.

That is, a bio optical signal from which a noise is removed by demodulating the bio optical signal based on a spreading code by the demodulator 130 may have a signal-to-noise ratio in proportion to the length of the spreading code.

Figure 12:
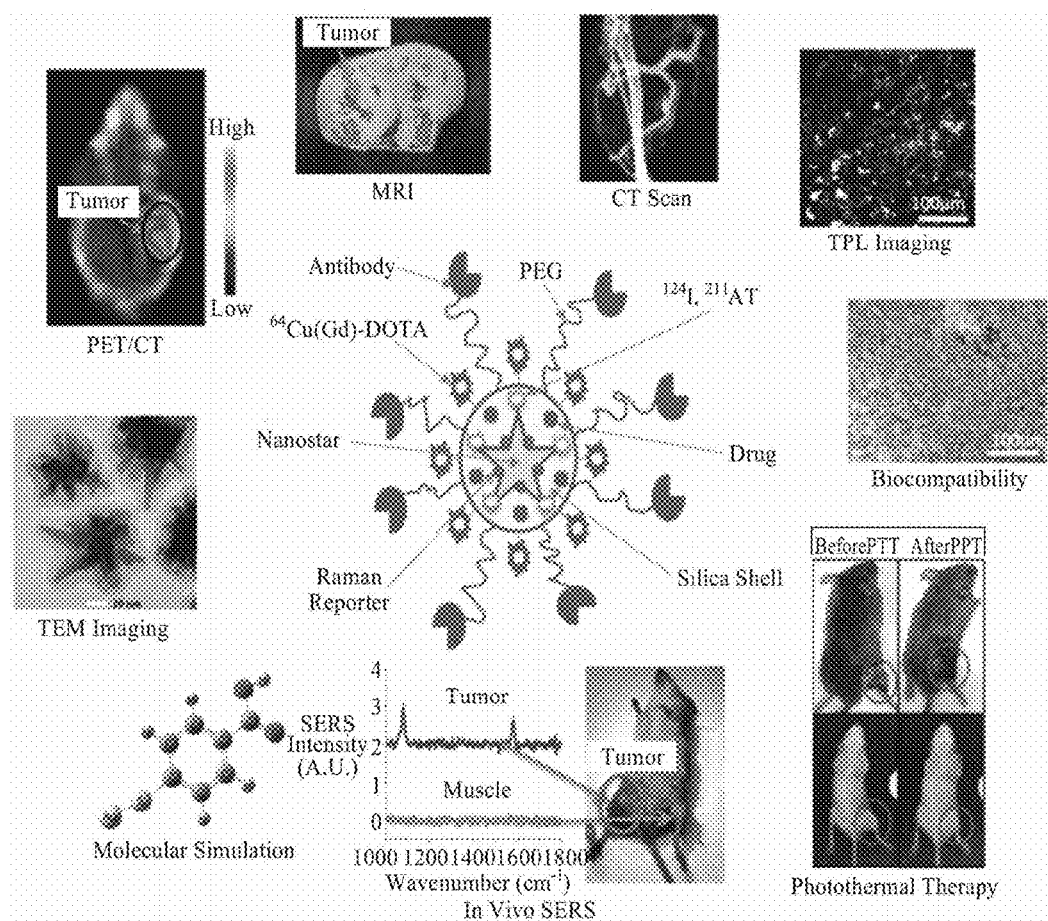
FIG. 12 illustrates bio sensing applications using a bio optical signal according to an example embodiment.

FIG. 12 illustrates results of processing a bio optical signal according to an example embodiment.

A bio optical signal processing apparatus may display a region corresponding to a target analyte in an image using a bio optical signal from which a noise is removed as illustrated in FIG. 12.

When a Raman scattering signal is used as a bio optical signal, the bio optical signal processing apparatus may search for a material corresponding to the Raman scattering signal from which the noise is removed by searching for a spectrum. In addition, the bio optical signal processing apparatus may generate an image based on a wavelength and an intensity of the Raman scattering signal from which the noise is removed in a video.

When a fluorescence scattering signal is used as a bio optical signal, the bio optical signal processing apparatus may map the fluorescence scattering signal from which noise is removed to an image based on a wavelength and an intensity of the fluorescence scattering signal from which a noise is removed in a video.

Although an accuracy of the Raman scattering signal is greater than an accuracy of the fluorescence scattering signal, an amount of time used to measure the Raman scattering signal may be greater than an amount of time used to measure the fluorescence scattering signal.

Because a color of the fluorescence scattering signal varies depending on a fluorescent material, the fluorescence scattering signal may be easy to be identified. However, the accuracy of the fluorescence scattering signal may be less than the accuracy of the Raman scattering signal. Thus, as a size of the target analyte decreases, a number of embodiments using the Raman scattering signal as the bio optical signal increases. As the size of the target analyte, for example, a cell, increases, a number of embodiments using the fluorescence scattering signal as the bio optical signal increases.

Figure 13:
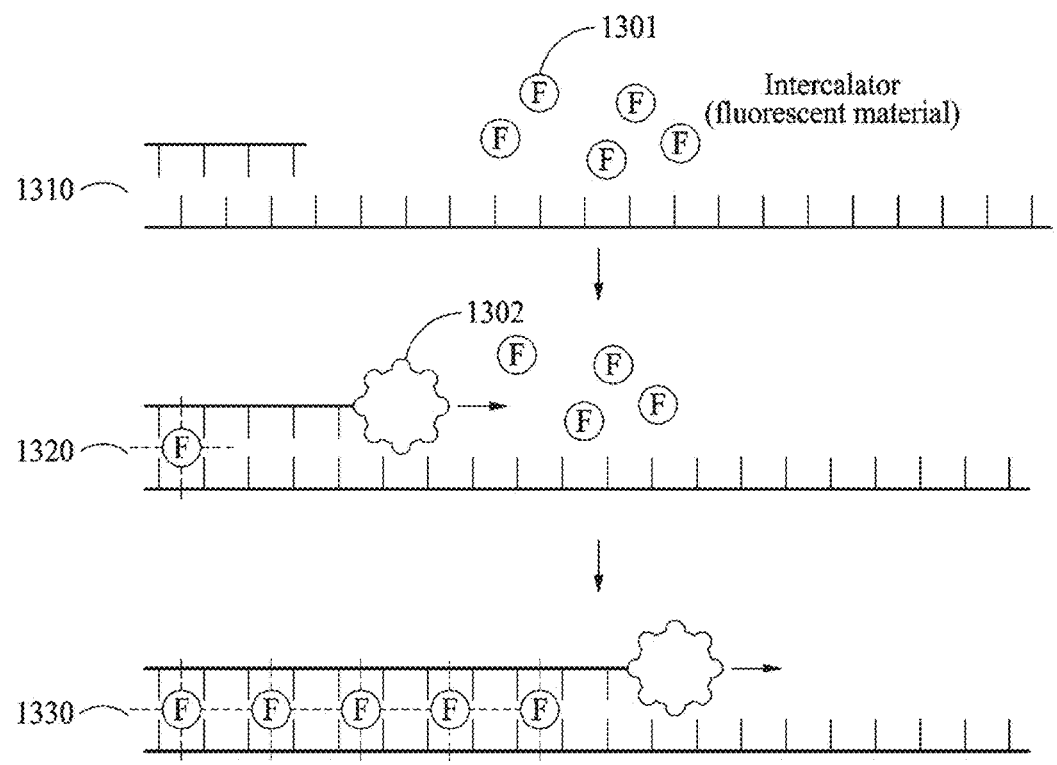
FIG. 13 illustrates a process of performing a fluorescence process on a target analyte according to an example embodiment.

FIG. 13 illustrates a process of performing a fluorescence process on a target analyte according to an example embodiment.

In an operation 1310, a bio optical signal processing apparatus denatures a primer to be a fluorescent material using an intercalator.

In operation 1320, the bio optical signal processing apparatus performs primer annealing for annealing a fluorescent material 1301 to a target analyte. Here, a Taq polymerase 1302 may prevent a denaturation caused by a heat occurring by repeating overheating and cooling in a process of a polymerase chain reaction.

In operation 1330, the bio optical signal processing apparatus applies the fluorescent material 1301 to the target analyte by extending a structure annealed in operation 1320.

Figure 14:
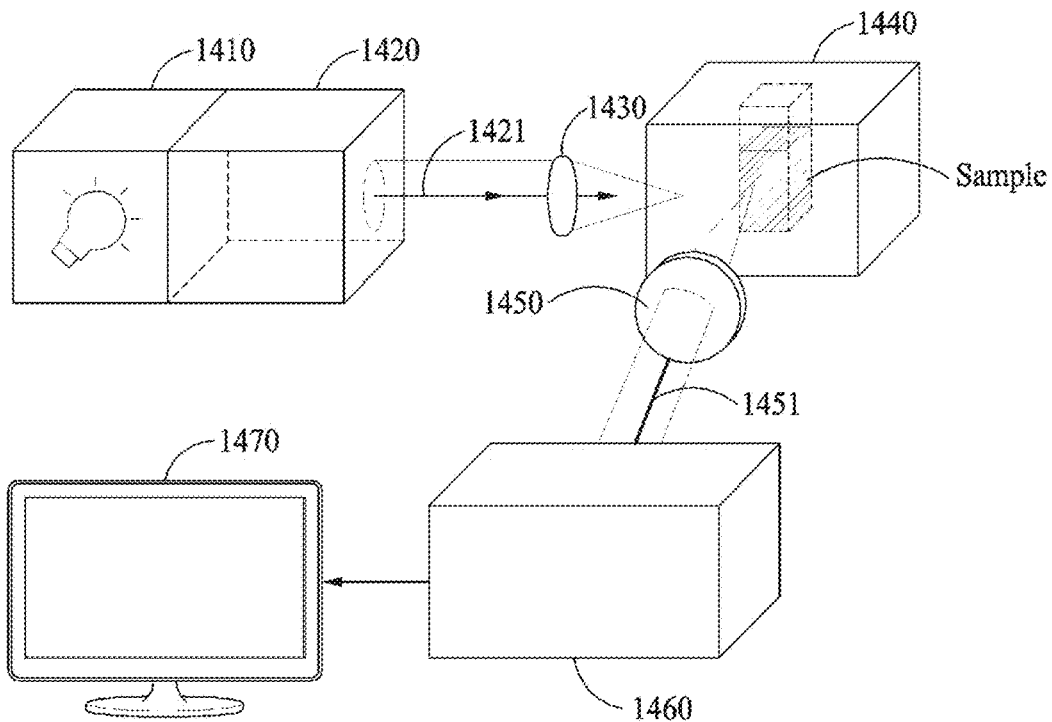
FIG. 14 illustrates a bio optical signal processing apparatus for processing a fluorescence signal according to an example embodiment.

FIG. 14 illustrates a bio optical signal processing apparatus for processing a fluorescence signal according to an example embodiment.

A light source 1410 emits an incident beam to a modulator 1420. Here, a width of a wavelength change in an incident beam and a width of an intensity change in the incident beam may be greater than a width of a wavelength change in an incident beam and a width of an intensity change in the incident beam for using a Raman scattering signal or a Rayleigh scattering signal.

The modulator 1420 outputs an incident beam modulated by spreading a band of the incident beam based on a spreading code.

The modulated incident beam 1421 may be concentrated on, from a first lens 1430, a target analyte 1440 to which a fluorescent material is applied. A fluorescence scattering signal 1451 output by converting the modulated incident beam 1421 into a wavelength corresponding to the fluorescent material may be incident to a demodulator 1460 through a second lens 1450.

The demodulator 1460 may remove a noise from the fluorescence scattering signal 1451 by demodulating the fluorescence scattering signal 1451 based on the spreading code 250 identical to that of the modulator 1420.

An imaging processor 1470 of the bio optical signal processing apparatus may map the fluorescence scattering signal 1451 from which a noise is removed to an image to be displayed based on a wavelength and an intensity of the fluorescence scattering signal 1451 from which the noise is removed in a video.

Figure 15:
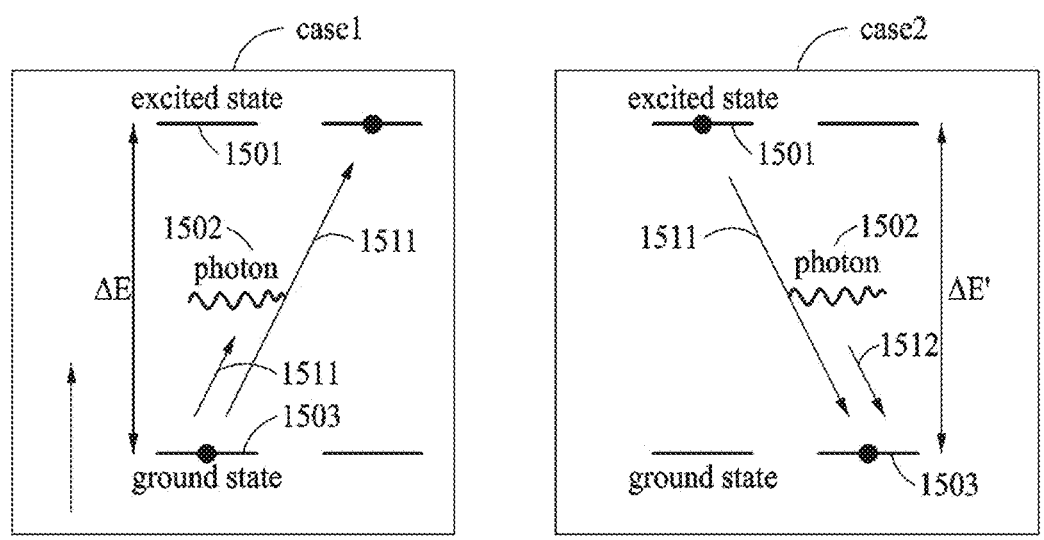
FIG. 15 illustrates a process of processing a bio optical signal according to an example embodiment.

FIG. 15 illustrates a process of processing a bio optical signal according to an example embodiment.

When the incident beam having photon energy 1502 entered a target analyte, the energy level of the target analyte may be transformed from a ground state 1503 to an excited state 1501 as shown in a case 1.

Because the excited state is unstable as shown in a case 2, the energy level may be transformed from the excited state 1501 to the ground state 1503, result in generation of fluorescence signal or Raman scattering signal.

Figure 16:
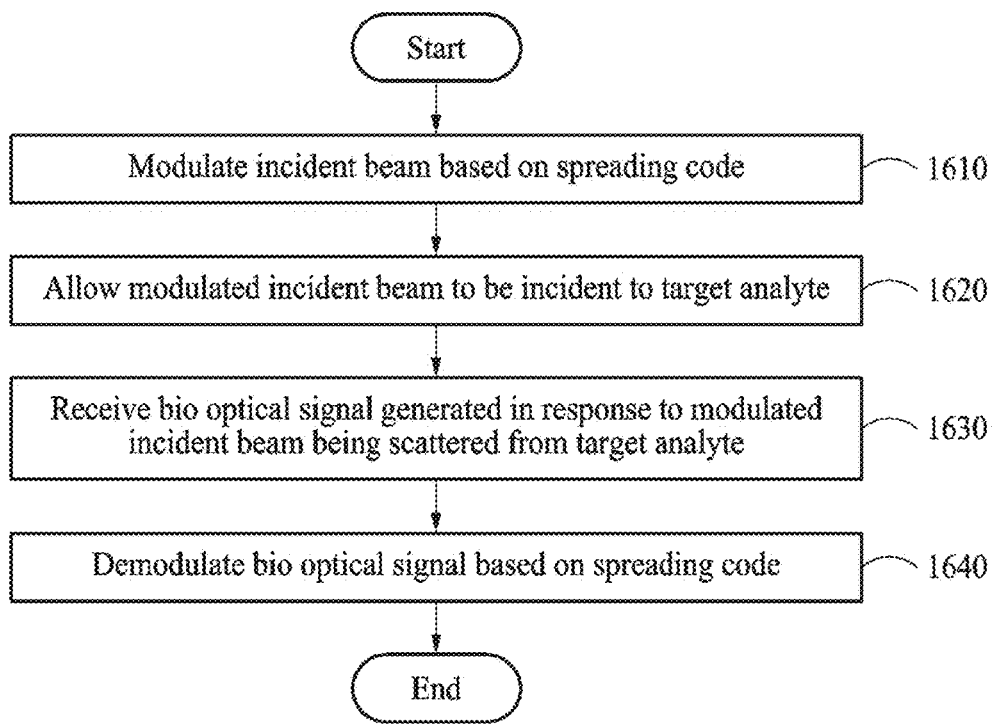
FIG. 16 is a flowchart illustrating a method of processing a bio optical signal according to an example embodiment.

FIG. 16 is a flowchart illustrating a method of processing a bio optical signal according to an example embodiment.

In operation 1610, the modulator 110 modulates an incident beam incident to the modulator 110 based on a spreading code.

In operation 1620, the modulator 110 allows the incident beam modulated in operation 1610 to be incident to the target analyte 120. Here, the modulated incident beam excites molecules of the target analyte 120 such that a bio optical signal may be generated.

In operation 1630, the demodulator 130 receives the bio optical signal generated in response to the modulated incident beam being scattered from the target analyte 120.

In operation 1640, the demodulator 130 demodulates the bio optical signal received in operation 1630 based on a spreading code identical to the spreading code used in operation 1610.

In more detail, the demodulator 130 may output a Raman scattering signal from which a noise is removed by demodulating the Raman scattering signal from a signal that is backscattered by a length of a code sequence of the spreading code.

According to example embodiments described herein, it is possible to improve a signal-to-noise ratio and a resolution of a bio optical signal by removing system noises, for example, a background fluorescence signal, by modulating an incident beam based on a spreading code, allowing the modulated incident beam to a target analyte, and demodulating a bio optical signal output from the target analyte using a spreading code identical to the spreading code used to modulate the incident beam.

The components described in the exemplary embodiments of the present invention may be achieved by hardware components including at least one DSP (Digital Signal Processor), a processor, a controller, an ASIC (Application Specific Integrated Circuit), a programmable logic element such as an FPGA (Field Programmable Gate Array), other electronic devices, and combinations thereof. At least some of the functions or the processes described in the exemplary embodiments of the present invention may be achieved by software, and the software may be recorded on a recording medium. The components, the functions, and the processes described in the exemplary embodiments of the present invention may be achieved by a combination of hardware and software.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An optical signal processing apparatus, comprising:
   a modulator configured to determine a modulation speed of an incident beam based on a lifetime of an optical signal, modulate the incident beam based on a spreading code and the determined modulation speed, and emit the modulated incident beam to an analyte,
   wherein the modulated incident beam is scattered by the analyte to generate the optical signal.

2. The optical signal processing apparatus of claim 1, wherein the modulator is further configured to modulate the incident beam using a frequency greater than a frequency of an auto-fluorescence signal, in response to the optical signal corresponding to a Raman scattering signal.

3. The optical signal processing apparatus of claim 1, wherein a width of a wavelength change in the incident beam and a width of an intensity change in the incident beam are determined based on a type of the optical signal.

4. The optical signal processing apparatus of claim 1, wherein the optical signal, which is demodulated based on the spreading code to remove noise from the bio optical signal, has a signal-to-noise ratio in proportion to a length of the spreading code.

5. The optical signal processing apparatus of claim 1, wherein
   the modulator is further configured to determine a first modulation speed, in response to a Raman scattering signal being used as the optical signal, and determine a second modulation speed, in response to a Rayleigh scattering signal being used as the optical signal, and
   the first modulation speed is greater than the second modulation speed.

6. The optical signal processing apparatus of claim 5, wherein
   the modulator is further configured to determine a third modulation speed, in response to a fluorescence scattering signal being used as the optical signal, and
   the second modulation speed is greater than the third modulation speed.

7. The optical signal processing method of claim 6, wherein the fluorescence scattering signal is generated in response to the incident beam being emitted to a fluorescent material.

8. The optical signal processing apparatus of claim 1, wherein the optical signal is correlated with the modulated incident beam.

9. The optical processing apparatus of claim 1, wherein the optical signal is demodulated based on the spreading code to remove noise from the optical signal.

10. The optical processing apparatus of claim 1, wherein the lifetime of the optical signal is based on a time period for a constituent of the analyte to transition from an exited state to a ground state.

11. An optical signal processing apparatus, comprising:
    a demodulator configured to collect an optical signal generated by an incident beam being scattered by an analyte, determine a demodulation speed based on a lifetime of the optical signal, and remove noise from the optical signal by demodulating the optical signal based on a spreading code and the determined demodulation speed,
    wherein the incident beam is modulated based on the spreading code wherein the optical signal is correlated with the modulated incident beam.

12. The optical signal processing apparatus of claim 11, wherein the demodulated optical signal has a signal-to-noise ratio in proportion to a length of the spreading code.

13. An optical signal processing apparatus, comprising:
- a modulator configured to determine a modulation speed of an incident beam based on a lifetime of an optical signal, modulate the incident beam based on a spreading code and the determined modulation speed, and emit the modulated incident beam to an analyte; and
- a demodulator configured to collect the optical signal, which is generated by the modulated incident beam being scattered from the target analyte, and remove noise from the optical signal by demodulating the optical signal based on the spreading code,
- wherein the optical signal is correlated with the modulated incident beam.

\* \* \* \* \*